under 35
U.S.C. 154(b) by 809 days.

(12) United States Patent
Aga

(10) Patent No.: US 9,204,816 B2
(45) Date of Patent: Dec. 8, 2015

(54) METHOD AND SYSTEM FOR DETERMINING BODY IMPEDANCE

(75) Inventor: Arshan Aga, Mountain View, CA (US)

(73) Assignee: VITAL CONNECT, INC., Campbell, CA (US)

( * ) Notice: Subject to any disclaimer, the term of this patent is extended or adjusted under 35 U.S.C. 154(b) by 809 days.

(21) Appl. No.: 13/419,218

(22) Filed: Mar. 13, 2012

(65) Prior Publication Data

US 2013/0245487 A1    Sep. 19, 2013

(51) Int. Cl.
*A61B 5/053*  (2006.01)
*A61B 5/00*  (2006.01)

(52) U.S. Cl.
CPC ............. *A61B 5/0537* (2013.01); *A61B 5/4875* (2013.01); *A61B 5/0531* (2013.01)

(58) Field of Classification Search
CPC ..... A61B 5/053; A61B 5/0531; A61B 5/0537
USPC ........................................................ 600/547
See application file for complete search history.

(56) References Cited

U.S. PATENT DOCUMENTS

| 7,184,820 | B2 | 2/2007 | Jersey-Willuhn et al. |  |
|---|---|---|---|---|
| 7,233,823 | B2 * | 6/2007 | Simond et al. | 600/547 |
| 7,701,227 | B2 * | 4/2010 | Saulnier et al. | 324/601 |
| 7,783,344 | B2 | 8/2010 | Lackey et al. |  |
| 8,632,473 | B2 * | 1/2014 | Sowelam | 600/538 |
| 8,909,333 | B2 * | 12/2014 | Rossi | 600/547 |
| 8,934,966 | B2 * | 1/2015 | Osawa | 600/547 |
| 8,965,497 | B2 * | 2/2015 | Tournefier et al. | 600/547 |

FOREIGN PATENT DOCUMENTS

| JP | Sho49-72093 | 10/1972 |
|---|---|---|
| WO | WO2005/018432 | 3/2005 |

OTHER PUBLICATIONS

PCT International Search Report and Written Opinion of the International Searching Authority, issued May 9, 2013, application No. PCT/US2013/025565.

* cited by examiner

*Primary Examiner* — Max Hindenburg
(74) *Attorney, Agent, or Firm* — Sawyer Law Group, P.C.

(57) ABSTRACT

A method and system for determining a body impedance ($Z_{body}$) of a user are disclosed. The method comprises coupling a sensor device to the user, wherein the sensor device includes at least a first and a second electrode. The method includes applying a voltage signal ($V_{in}$) through a first impedance ($Z_{in1}$) to the first electrode and through a second impedance ($Z_{in2}$) to the second electrode to produce an output signal. The method includes measuring a differential voltage ($V_{body}$) across the first and second electrodes and calculating the body impedance ($Z_{body}$) using the measured differential voltage ($V_{body}$), the voltage signal ($V_{in}$), the first impedance ($Z_{in1}$), and the second impedance ($Z_{in2}$).

20 Claims, 11 Drawing Sheets

METHOD AND SYSTEM FOR DETERMINING BODY IMPEDANCE

FIELD OF THE INVENTION

The present invention relates to sensor devices, and more particularly, to a method and system for determining body impedance using a sensor device.

BACKGROUND

Approximately 60% of an average person's body weight is composed of water. A person's body weight composition varies due to a variety of factors including age, diet, weight, and gender. Despite these variations, the majority of a person's body weight composition is made up of water. Physiologically, "body water" or "hydration level" are terms utilized to describe the water content of the body. A person's hydration level can be described in liters or as a percentage of the person's total body weight.

Maintaining a reasonable and healthy hydration level is crucial to the overall health of a person. Additionally, even small decreases in a person's hydration level can significantly affect athletic performance levels. Conventional methods of testing a body's hydration level include monitoring body mass changes and testing blood and urine for various markers. However, these conventional methods are inefficient, costly and require time consuming laboratory analysis to arrive at the proper hydration level.

These issues limit the monitoring of a person's hydration level. Therefore, there is a strong need for a cost-effective solution that overcomes the above issues by non-invasively calculating body impedance in real-time using sensor devices to enable the monitoring of health related values. The present invention addresses such a need.

SUMMARY OF THE INVENTION

A method and system for determining a body impedance ($Z_{body}$) of a user are disclosed. The method comprises coupling a sensor device to the user, wherein the sensor device includes at least a first and a second electrode. The method includes applying a voltage signal ($V_{in}$) through a first impedance ($Z_{in1}$) to the first electrode and through a second impedance ($Z_{in2}$) to the second electrode to produce an output signal. The method includes measuring a differential voltage ($V_{body}$) across the first and second electrodes and calculating the body impedance ($Z_{body}$) using the measured differential voltage ($V_{body}$), the voltage signal ($V_{in}$), the first impedance ($Z_{in1}$), and the second impedance ($Z_{in2}$).

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

Figure 1:
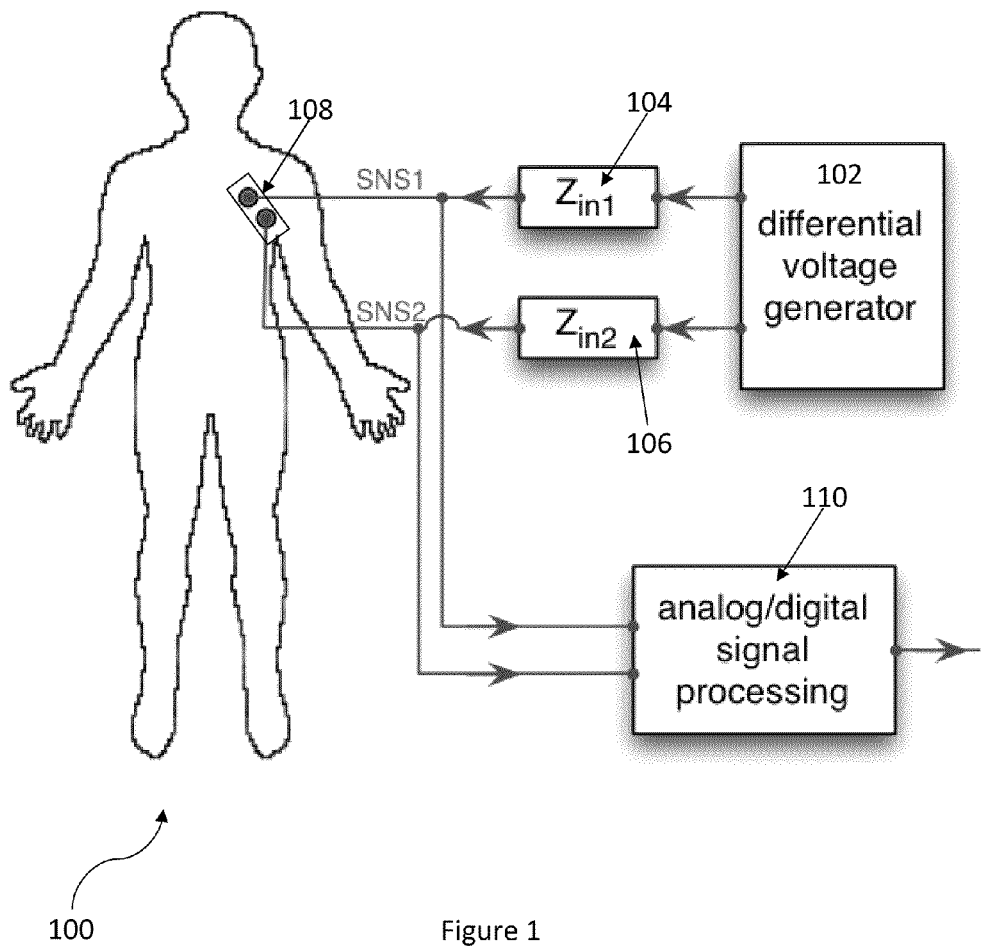
FIG. 1 illustrates a differential system in accordance with a first embodiment.

The present invention relates to sensor devices, and more particularly, to a method and system for determining body impedance using a sensor device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention allows for the measurement of a user's body impedance using a sensor device. One of ordinary skill in the art readily recognizes that a variety of sensor devices may be utilized including wireless sensor devices with embedded circuitry and that would be within the spirit and scope of the present invention. By connecting a portable sensor device to the user through two or more sensor nodes or electrodes and stimulating these sensor nodes with an electrical signal through a known impedance, a resultant electrical output signal at the sensor nodes is detected by the portable sensor device. The resultant electrical output signal is processed using a combination of analog and digital signal processing to determine the impedance of the user's body or body impedance ($Z_{body}$).

The determined body impedance ($Z_{body}$) is further processed using a hardware and/or software approach to determine a health related value such as the hydration level of the user. One of ordinary skill in the art readily recognizes that the calculated body impedance can be utilized for measuring and/or monitoring a variety of health related values including but not limited to a person's hydration levels and respiratory rates and that would be within the spirit and scope of the present invention.

In one embodiment, the impedance from one location of a user's body to another location of the user's body, or body impedance, is known as $Z_{body}$. $Z_{body}$ is inversely proportional to the level of hydration per the following equation:

$$\text{Hydration Level } \alpha \, 1/Z_{body}.$$

Using this inverse relationship, $Z_{body}$ is converted into a user's hydration level through hardware configurations and/or software algorithms that include other variables such as age, height, race, diet, weight, and gender. $Z_{body}$ is measured by injecting an input voltage signal ($V_{in}$) through a known impedance ($Z_{in}$) and through two or more electrodes into the user's body which has an unknown body impedance ($Z_{body}$). Given that $V_{in}$ and $Z_{in}$ are known values and that the voltage ($V_{body}$) across $Z_{body}$ can be measured by a sensor device, $Z_{body}$ is the only unknown value that needs to be calculated per the following equation:

$$Z_{body} = (V_{body}/(V_{in} - V_{body})) \times Z_{in}.$$

In one embodiment, the change in the calculated $Z_{body}$ value is utilized to measure respiration rate and respiration depth. When a person inhales and air fills up the lungs, the impedance across the person's lungs increases. When the person exhales and there is less air in the lungs, the impedance across the person's lungs decreases. By placing two or more electrodes on a user's body around the lungs, the voltage ($V_{body}$) across $Z_{body}$ can be measured by a sensor device once again to allow for the calculation of $Z_{body}$. $Z_{body}$ is directly proportional to the air in the lungs per the following equation:

$$\text{Air in Lungs } \alpha Z_{body}.$$

One of ordinary skill in the art readily recognizes that the input voltage signal ($V_{in}$) can be a variety of types of signals including but not limited to a single ended signal, a differential signal that can be inputted at different locations on the user's body, or a differential signal that can be inputted at different times or simultaneously and that would be within the spirit and scope of the present invention. Additionally, one of ordinary skill in the art readily recognizes that the input voltage signal ($V_{in}$) can be inputted on multiple electrodes which would create multiple differential voltages requiring additional calculations to find $Z_{body}$ and that would be within the spirit and scope of the present invention.

One of ordinary skill in the art readily recognizes that the known impedance ($Z_{in}$) can be a variety of impedances including but not limited to any combination of resistors, capacitors, inductors, switches, and transformer elements either in series or in parallel combinations to form an impedance that is deterministic in nature and that would be within the spirit and scope of the present invention.

To measure $Z_{body}$ more accurately, one of ordinary skill in the art readily recognizes that the input voltage signal ($V_{in}$) can be a square wave or a pulsed signal with fast rise and fall times that are less than 50 nanoseconds (ns) to reduce and make negligible the impedance of the two or more electrodes and that would be within the spirit and scope of the present invention.

As aforementioned, the resultant electrical output signal is processed to remove noise and/or artifacts such as bodily movements using a variety of hardware and/or software approaches including but not limited to a processing unit with circuits that perform functions such as rectification, absolute value, sample-and-hold, and track-and-hold. The processing unit can be a separate device coupled to the portable sensor device or can be entirely and/or partially embedded within the portable sensor device. These circuits may cause transitions or glitches in the output signal produced when the input voltage signal ($V_{in}$) or a circuit clock transitions. One of ordinary skill in the art readily recognizes that a common analog circuit block can be used after these circuits to reduce and/or eliminate the effects of these glitches or transitions and that would be within the spirit and scope of the present invention.

One of ordinary skill in the art readily recognizes that the common analog circuit block can be a variety of devices including but not limited to a filter that suppresses sharp transitions or a sampling circuit that has a clock with correct phase and/or correct duty cycle so the glitches or transitions are not detected by subsequent circuit blocks and that would be within the spirit and scope of the present invention. Additionally, one of ordinary skill in the art readily recognizes that the clock within each circuit block of the processing unit can have a variety of features including but not limited to programmable phase shifts, being phase shifted with respect to one another, and being non-overlapping with respect to one another through phase shifting, duty cycle alterations, or programmability and that would be within the spirit and scope of the present invention.

In addition to the glitches or transitions in the output signal, one of ordinary skill in the art readily recognizes that the processing unit can experience a variety of circuit non-idealities including but not limited to voltage driver pull-up and pull-down impedances and/or transition times being mismatched, a duty cycle of the voltage driver pull-up and pull-down not being ideal, the voltage driver not being completely differential due to a mismatch or by design, offsets in the various circuit blocks, and various circuit clocks being out of phase due to variations or by design and that would be within the spirit and scope of the present invention. These circuit non-idealities can be overcome by performing analog and/or digital processing including but not limited to circuit calibrations, adding switches, and programmatically altering any of the circuit blocks and that would be within the spirit and scope of the present invention.

The body impedance ($Z_{body}$) can be used to determine the absolute level of hydration in the user and/or to determine a relative level of hydration in the user. Determining a relative level of hydration in the user enables variations above certain thresholds to signify changes in the condition of the user between various levels including but not limited to slightly dehydrated, moderately dehydrated, severely dehydrated, and over-hydrated and that would be within the spirit and scope of the present invention.

To describe the features of the present invention in more detail, refer now to the following description in conjunction with the accompanying Figures.

FIG. 1 illustrates a differential system 100 in accordance with a first embodiment. The differential system 100 includes a differential voltage generator 102, a first impedance unit 104 ($Z_{in1}$) and a second impedance unit 106 ($Z_{in2}$) both coupled to the differential voltage generator 102, a sensor device 108 with a first electrode (SNS1) coupled to the first impedance 104 and with a second electrode (SNS2) coupled to the second impedance 106, and an analog/digital signal processing unit 110 coupled to the sensor device 108.

One of ordinary skill in the art readily recognizes that the differential system 100 can utilize more than two impedance units and electrodes and that would be within the spirit and scope of the present invention. Additionally, one of ordinary skill in the art readily recognizes that the analog/digital signal processing unit 110 can also be embedded entirely or partially within the sensor device 108 and that would be within the spirit and scope of the present invention. Additionally, one of ordinary skill in the art readily recognizes that the differential system 100 can utilize a variety of voltage sources including but not limited to voltage generators and current sources and that would be within the spirit and scope of the present invention.

The sensor device 108 is coupled to a user of the differential system 100. The differential voltage generator 102 provides stimulus to the sensor device 108. In one embodiment, the differential voltage generator 102 transitions from a high voltage level to a low voltage level. One of ordinary skill in the art readily recognizes that the differential voltage generator 102 high and low voltage levels can be accomplished in a variety of ways including but not limited to a supply and ground voltage, a battery and ground voltage, or a positive and negative supply and that would be within the spirit and scope of the present invention.

Additionally, one of ordinary skill in the art readily recognizes that the differential voltage generator 102 high and low voltage levels can be accomplished by deriving two voltage levels from a positive supply or battery and a negative supply or ground through any combination of the means of regulation, charge pump regulation, voltage division or a ground derived through means such as regulation or voltage dividers and that would be within the spirit and scope of the present invention.

In one embodiment, the stimulus provided by the differential voltage generator 102 is a square or pulse wave with a frequency of 1 megahertz (MHz) with sharp transition times between the high voltage level and the low voltage level. One of ordinary skill in the art readily recognizes that the stimulus can be a variety of other frequencies including but not limited to frequencies greater than 500 kilohertz (kHz) and can be a variety of other types of waves that exhibit sharp transition times that are less than 50 ns and that would be within the spirit and scope of the present invention.

A differential voltage amplitude or peak is sensed by the first and second electrodes of the sensor device 108 due to a voltage divider created between the first and second impedances 104-106 and the body impedance of the user. The differential voltage is processed by the analog/digital signal processing unit 110 utilizing analog and/or digital processing functions which results in a resultant value. One of ordinary skill in the art readily recognizes that a variety of analog and/or digital processing functions can be utilized including but not limited to a rectifier, an absolute value=|x|, a squaring function=$x^2$, sampling, sample-and-hold, track-and-hold, analog filtering, analog equalization, amplification, digitizing with an analog-to-digital converter, digital filtering, digital amplification, artifact removal, and baseline wander removal and that would be within the spirit and scope of the present invention.

One of ordinary skill in the art readily recognizes that the resultant value of the differential voltage post processing represents the body impedance that is inversely proportional to the level of hydration or level of water in the user's body and that would be within the spirit and scope of the present invention.

Figure 2:
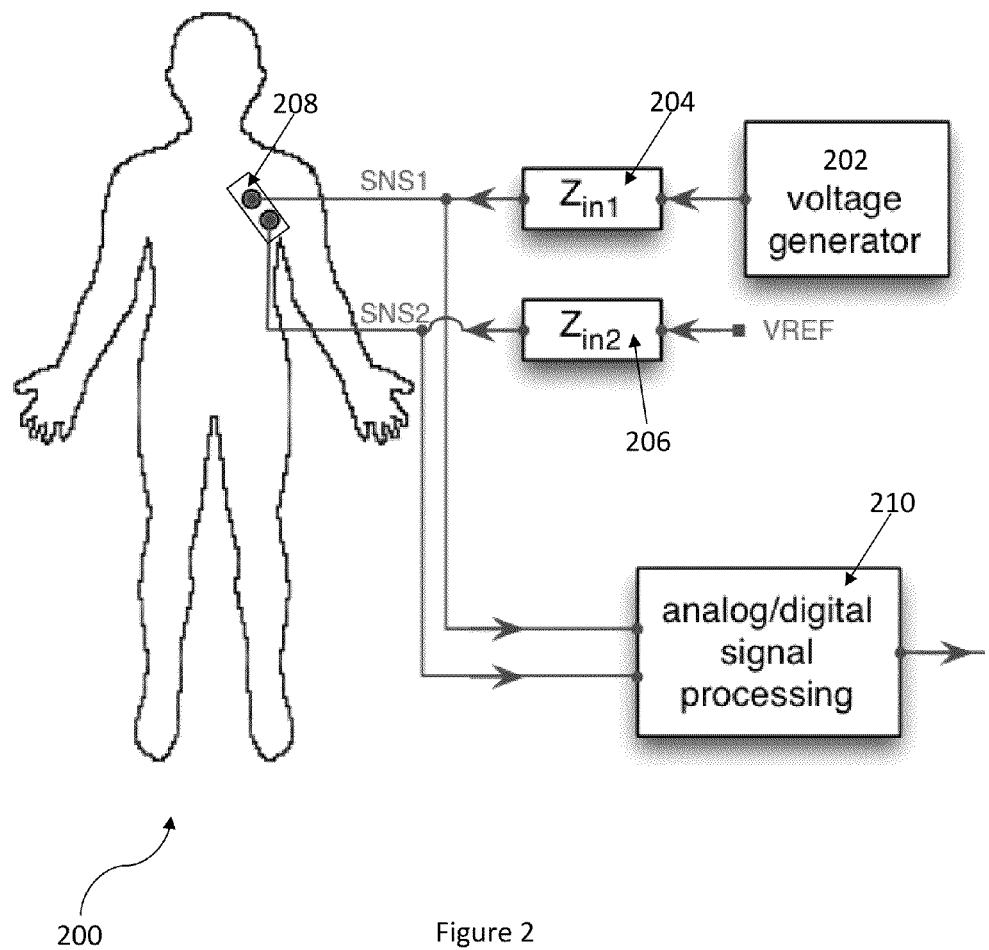
FIG. 2 illustrates a single-ended system in accordance with a first embodiment.

FIG. 2 illustrates a single-ended system 200 in accordance with a first embodiment. The single-ended system 200 includes a voltage generator 202, a first impedance unit 204 ($Z_{in1}$) coupled to the voltage generator 202, a second impedance unit 206 ($Z_{in2}$) coupled to a reference voltage ($V_{ref}$), a sensor device 208 with a first electrode (SNS1) coupled to the first impedance 204 and with a second electrode (SNS2) coupled to the second impedance 206, and an analog/digital signal processing unit 110 coupled to the sensor device 208.

Accordingly, the single-ended system 200 resembles the configuration of the differential system 100 except that in the single-ended system 200, the voltage generator 202 inputs a voltage square or pulse wave into the first electrode (SNS1) of the sensor device 208 while the second electrode (SNS2) of the sensor device 108 is held at a constant reference voltage ($V_{ref}$). Current flows in and out of the second electrode of the sensor device 208 that is held at $V_{ref}$. Based on a voltage divider between the first and second impedances 204-206 and the voltage across the sensor device 208, the body impedance ($Z_{body}$) is calculated.

Figure 3:
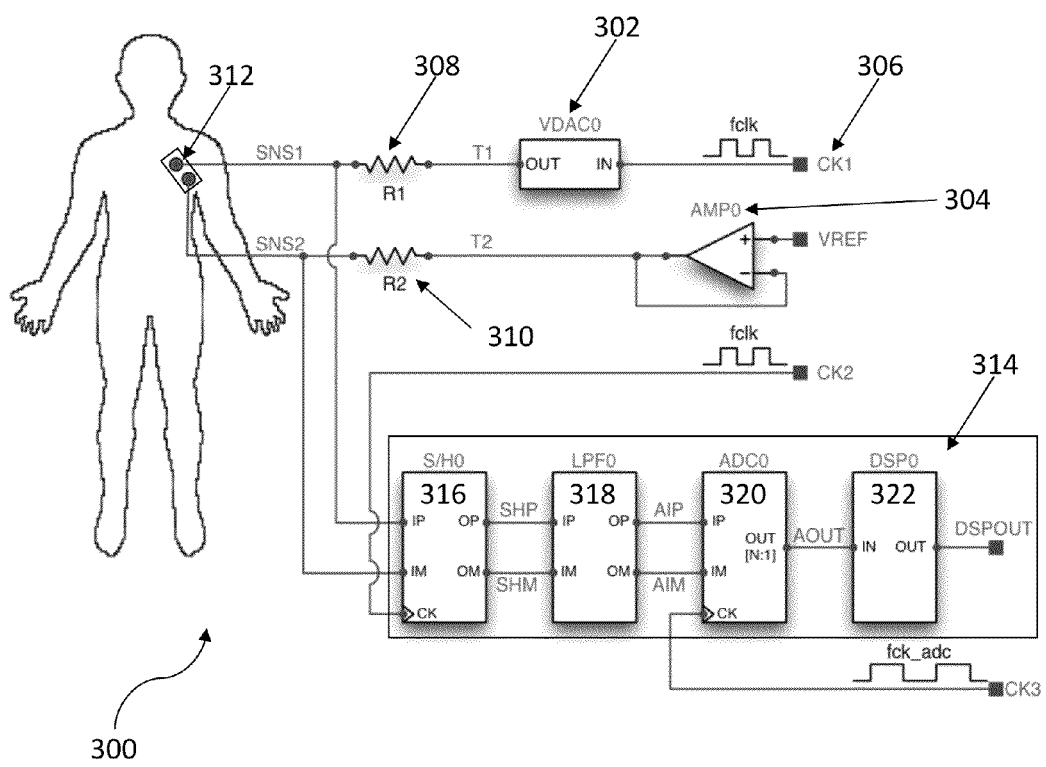
FIG. 3 illustrates a single-end system in accordance with a second embodiment.

FIG. 3 illustrates a single-ended system 300 in accordance with a second embodiment. The single-ended system 300 includes a voltage digital-to-analog converter (VDAC0 or voltage DAC) 302 and an amplifier (AMP0) 304, a first clock (CK1) 306 coupled to an input of the voltage DAC 302, a first resistor (R1) 308 coupled to an output of the voltage DAC 302, a second resistor (R2) 310 coupled to the amplifier 304, a sensor device 312 with a first electrode (SNS1) coupled to the first resistor 308 and with a second electrode (SNS2) coupled to the second resistor 310, and an analog/digital signal processing unit 314 coupled to the sensor device 312.

In the single-sided system 300, the first and second resistors 308-310 are the impedance units $Z_{in1}$ and $Z_{in2}$. One of ordinary skill in the art readily recognizes that the first and second resistors 308-310 can have a variety of resistance values that are precisely and accurately known including but not limited to having equal resistances to each other or having different resistances to each other and that would be within the spirit and scope of the present invention.

The analog/digital signal processing unit 314 includes a sample-and-hold function circuit (S/H0) 316, a low pass filter (LPF0) 318 coupled to the S/H0 316, an analog-to-digital converter (ADC0) 320 coupled to the LPF0 318, and a digital signal processor (DSP0) 322 coupled to the ADC0 320. One of ordinary skill in the art readily recognizes that the S/H0 316, LPF0 318, ADC0 320, and DSP0 322 can include a variety of configurations including but not limited to differential form with a plus and minus input/output configuration and that would be within the spirit and scope of the present invention.

In one embodiment, the S/H0 316 includes a first input (IP), a second input (IM), a first output (OP), a second output (OM), and a second clock (CK2). The LPF0 318 includes a first input (IP), a second input (IM), a first output (OP), and a second output (OM). The ADC0 320 includes a first input (IP), a second input (IM), an output (OUT [N:1]), and a third clock (CK3). The DSP0 322 includes an input (IN) and an output (OUT).

In the single-ended system 300, the first clock (CK1) 306 drives the input signal into the voltage DAC 302 and switches at frequency fclk to enable the voltage DAC 302 to switch the output to the first electrode of the sensor device 312 from a high voltage level to a low voltage level. One of ordinary skill in the art readily recognizes that the high voltage and low voltage levels can derive from a variety of sources including but not limited to a supply and a ground through regulation or voltage dividers or both and that would be within the spirit and scope of the present invention. In one embodiment, the voltage DAC 302 is a simple digital inverter or buffer that switches between supply and ground.

The second electrode of the sensor device 312 is held at a constant reference voltage ($V_{ref}$) by the amplifier 304 in a voltage follower configuration. One of ordinary skill in the art readily recognizes that the voltage follower configuration can be a variety of configurations that maintain a constant value close to $V_{ref}$ and that have current flowing in and out including but not limited to $V_{ref}=((VDAC\_HI+VDAC\_LO)/2)$ and that would be within the spirit and scope of the present invention.

After the first and second electrodes of the sensor device 312 receive the input voltages from the voltage DAC 302 and the amplifier 304, an amplitude of a resultant square or pulse wave voltage signal ($V_{body}$) across $Z_{body}$ caused by a voltage divider between the first and second resistors 308-310 and the body impedance ($Z_{body}$) is detected by the sensor device 312 across the first and second electrodes. The resultant square or pulse wave voltage signal is coupled to the analog/digital signal processing unit 314 for processing. Accordingly, the resultant square or pulse wave voltage signal serves as an input signal to the analog/digital signal processing unit 314.

In the analog/digital signal processing unit 314, the resultant square or pulse wave voltage signal is processed by the S/H0 316 and the second clock (CK2) using a square or pulse wave at a frequency fclk. In one embodiment, the second clock (CK2) is in phase with the first clock (CK1) 306. If the phases of CK1 and CK2 are done correctly such that the value held by the output of the S/H0 316 corresponds to either the positive or negative amplitude of the resultant square or pulsed wave voltage signal, the output of the S/H0 316 is a voltage value that is related to the body impedance ($Z_{body}$) value with additional unwanted noise or rippling or artifacts produced by the sensor device 312.

In the analog/digital signal processing unit 314, the outputs (SHP/SHM) of the S/H0 316 are filtered and/or amplified by the LPF0 318. One of ordinary skill in the art readily recognizes that the LPF0 318 can be comprised of a variety of filters including but not limited to a low pass filter, a high pass filter, a band-pass filter, or a band-reject filter and that would be within the spirit and scope of the present invention. The outputs of the LPF0 318 (AlP/AIM) are digitized by the ADC0 320 that is clocked at fck_adc via the third clock (CK3). In one embodiment, the ADC0 320 is an N-bit analog-to-digital converter (ADC).

The output (AOUT) of the ADC0 320 is processed by the DSP0 322 by performing at least one of a variety of functions including but not limited to filtering the signal, equalizing the signal, removing any artifacts, removing baseline wander, amplifying the signal, or performing mathematical operations on the signal to find an output (DSPOUT) that is a clean body impedance ($Z_{body}$) value that does not contain artifacts due to motion, baseline wander, glitches, offsets and/or excessive noise. In one embodiment, the DSP0 322 further processes the output (AOUT) signal using user information including but not limited to age, height, race, diet, weight, gender, distance between electrodes, and previously recorded and/or stored data to output a variety of user related calculations including but not limited to hydration level, water content, respiration rate, and/or respiration depth.

Figure 4:
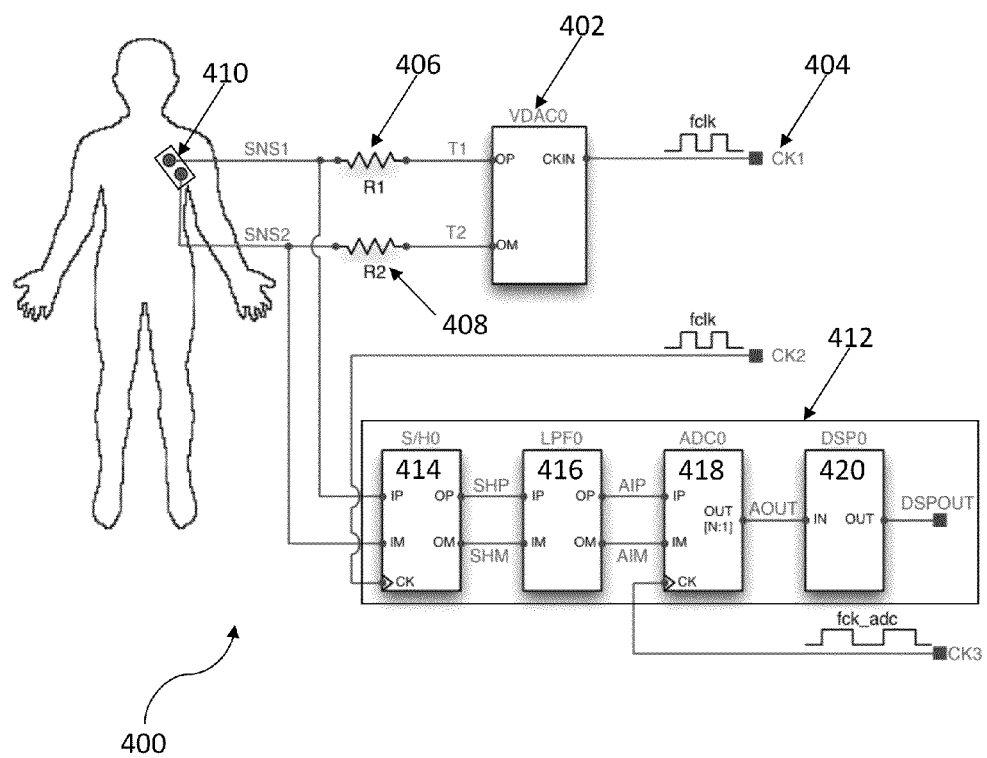
FIG. 4 illustrates a differential system in accordance with a second embodiment.

FIG. 4 illustrates a differential system 400 in accordance with a second embodiment. The differential system 400 includes a voltage digital-to-analog converter (VDAC0 or voltage DAC) 402, a first clock (CK1) 404 coupled to an input of the voltage DAC 402, a first resistor (R1) 406 coupled to an output (OP) of the voltage DAC 402, a second resistor (R2) 408 coupled to an output (OM) of the voltage DAC 402, a sensor device 410 with a first electrode (SNS1) coupled to the first resistor 406 and with a second electrode (SNS2) coupled to the second resistor 408, and an analog/digital signal processing unit 412 coupled to the sensor device 410.

The analog/digital signal processing unit 412 includes a sample-and-hold function circuit (S/H0) 414, a low pass filter (LPF0) 416 coupled to the S/H0 414, an analog-to-digital converter (ADC0) 418 coupled to the LPF0 416, and a digital signal processor (DSP0) 420 coupled to the ADC0 418. One of ordinary skill in the art readily recognizes that the S/H0 414, LPF0 416, ADC0 418, and DSP0 420 can include a variety of configurations and that would be within the spirit and scope of the present invention.

Accordingly, the differential system 400 resembles the configuration of the single-ended system 300 except that the differential system 400 does not include an amplifier. Instead, in the differential system 400, the voltage digital-to-analog converter (VDAC0 or voltage DAC) 402 outputs an electrical voltage signal differentially into the first and second electrodes of the sensor device 412. One of ordinary skill in the art readily recognizes that the voltage DAC 402 can include a variety of configurations including but not limited to two inverters or buffers that are driven by the first clock (CK1) 406 and an inverted version of CK1 that switches between supply and ground and that would be within the spirit and scope of the present invention.

One of ordinary skill in the art readily recognizes that the analog/digital signal process unit 412 can include a variety of circuit block configurations and that would be within the spirit and scope of the present invention.

Figure 5:
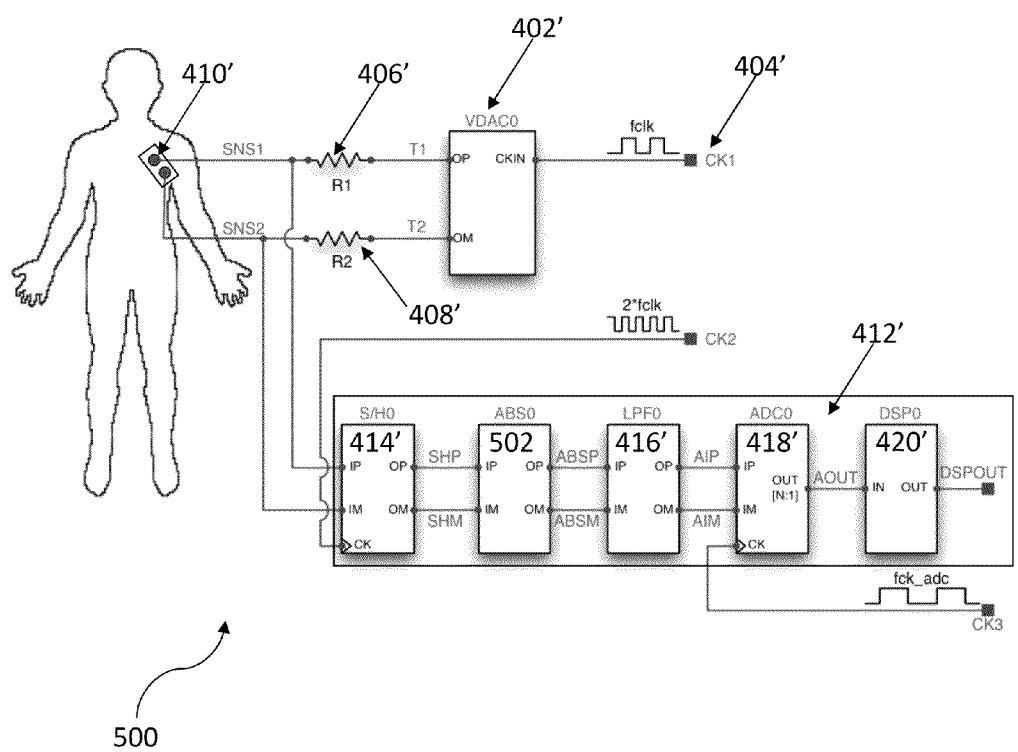
FIG. 5 illustrates a differential system in accordance with a third embodiment.

FIG. 5 illustrates a differential system 500 in accordance with a third embodiment. The differential system 500 is substantially similar to the differential system 400 except that the sample-and-hold circuit (S/H0) 414' is clocked at two times fclk (2*flck) via the second clock (CK2) and samples both the positive amplitude and the negative amplitude of the input signal in an alternate fashion.

Additionally, the analog/digital signal processing unit 412' further includes an absolute value circuit (ABS0) 502. The ABS0 502 includes a first input (IP), a second input (IM), a first output (OP), and a second output (OM). In one embodiment, the ABS0 502 takes an absolute value of the output signal of the S/H0 414' which rectifies the signal and makes the negative amplitude at the input a positive value at the output.

Thus, unlike the differential system 400 where only half the information is collected (either the positive or negative amplitude) while the other half of information is disregarded, the differential system 500 collects both the positive and negative amplitudes and rectifies them to output a positive value with twice as many samples over a given time period as the resultant output.

Figure 6:
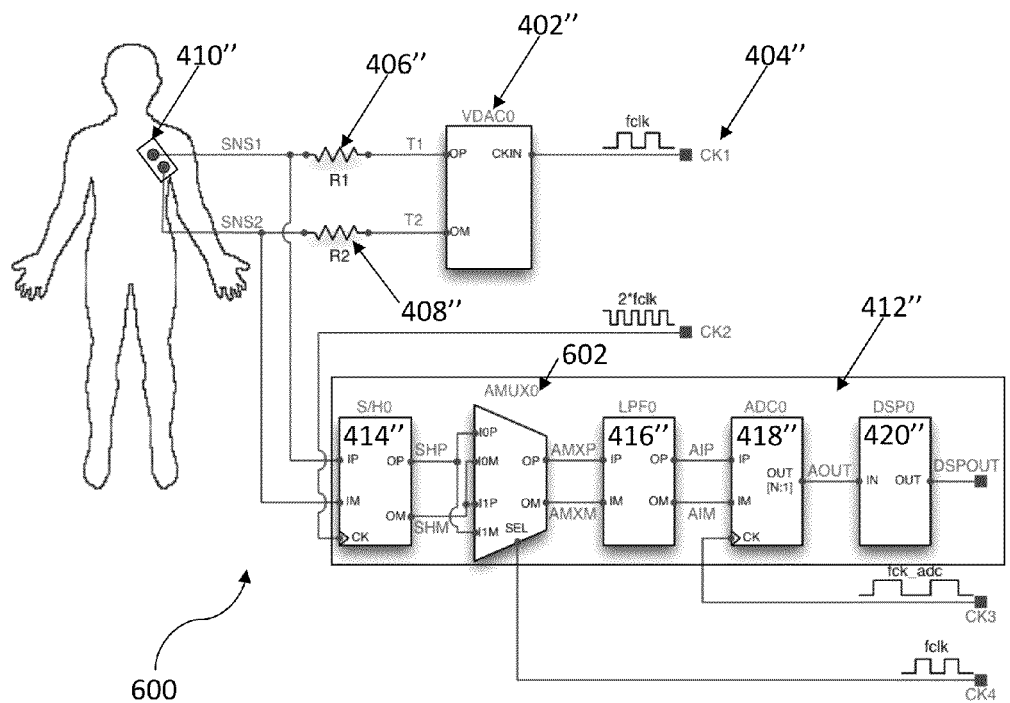
FIG. 6 illustrates a differential system in accordance with a fourth embodiment.

FIG. 6 illustrates a differential system 600 in accordance with a fourth embodiment. The differential system 600 is substantially similar to the differential system 500 except that the absolute value circuit 502 is implemented via an analog multiplexer (AMUX0) 602. The AMUX0 602 includes a first input (I0P), a second input (I0M), a third input (I1P), a fourth input (I1M), a first output (OP), a second output (OM), and a selector (SEL).

In one embodiment, the AMUX0 602 utilizes analog switches to connect the SHP input from the S/H0 414" and output AMXP and to connect the SHM input from the S/H0 414" and output AMXM when the fourth clock (CK4) is at a logical high level. When the CK4 is at a logical low level, the AMUX0 602 utilizes analog switches to connect the SHM input from the S/H0 414" and output AMXP and to connect the SHP input from the S/H0 414" and output AMXM. Accordingly, the AMUX0 602 implements the absolute value or rectifier function of the analog/digital signal processing unit 412".

Figure 7:
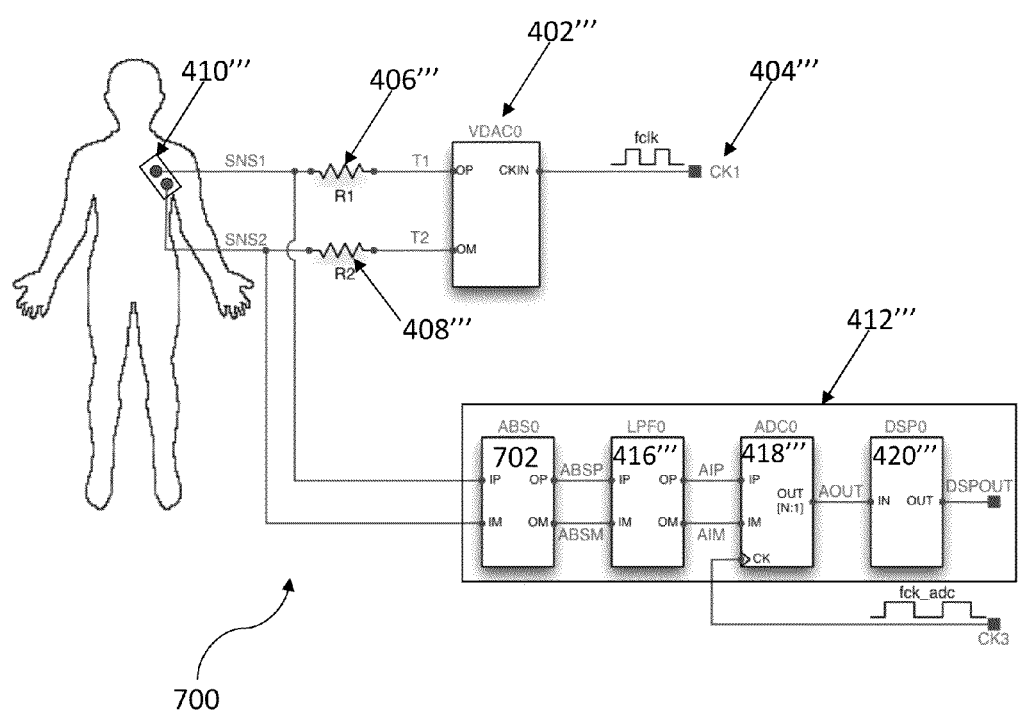
FIG. 7 illustrates a differential system in accordance with a fifth embodiment.

FIG. 7 illustrates a differential system 700 in accordance with a fifth embodiment. The differential system 700 is substantially similar to the differential system 400 except that the S/H0 414 circuit block is replaced with an absolute value circuit (ABS0) 702 in the analog/digital processing unit 412'''. The ABS0 702 utilizes an asynchronous absolute value instead of a clocked system with sample-and-hold or track-and-hold to process the resultant square or pulse wave voltage signal.

Figure 8:
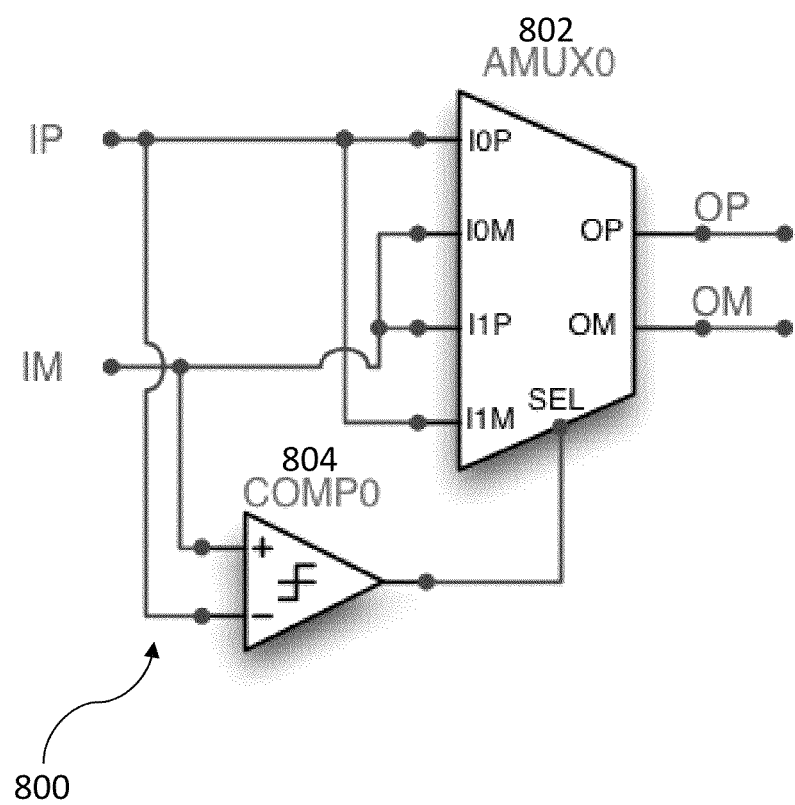
FIG. 8 illustrates an absolute value implementation in accordance with an embodiment.

FIG. 8 illustrates an absolute value implementation 800 in accordance with an embodiment. The absolute value implementation 800 includes a multiplexer (AMUX0) 802 and a comparator (COMP0) 804. The AMUX0 802 includes a first input (I0P), a second input (I0M), a third input (I1P), a fourth input (I1M), a first output (OP), a second output (OM), and a selector (SEL). The COMP0 804 includes a positive (+) and a negative (−) input and an output. The COMP0 804 senses when IP is greater than or less than IM to switch on the AMUX0 802 which implements the absolute value function of the analog/digital signal processing unit 412.

One of ordinary skill in the art readily recognizes that different types of multiplexers and comparators can be utilized by the absolute value implementation 800 including but not limited to an analog comparator or a clocked comparator and that would be within the spirit and scope of the present invention. Additionally, one of ordinary skill in the art readily recognizes that the multiplexor itself may be clocked eliminating the usage of a comparator and that would be within the spirit and scope of the present invention.

Figure 9:
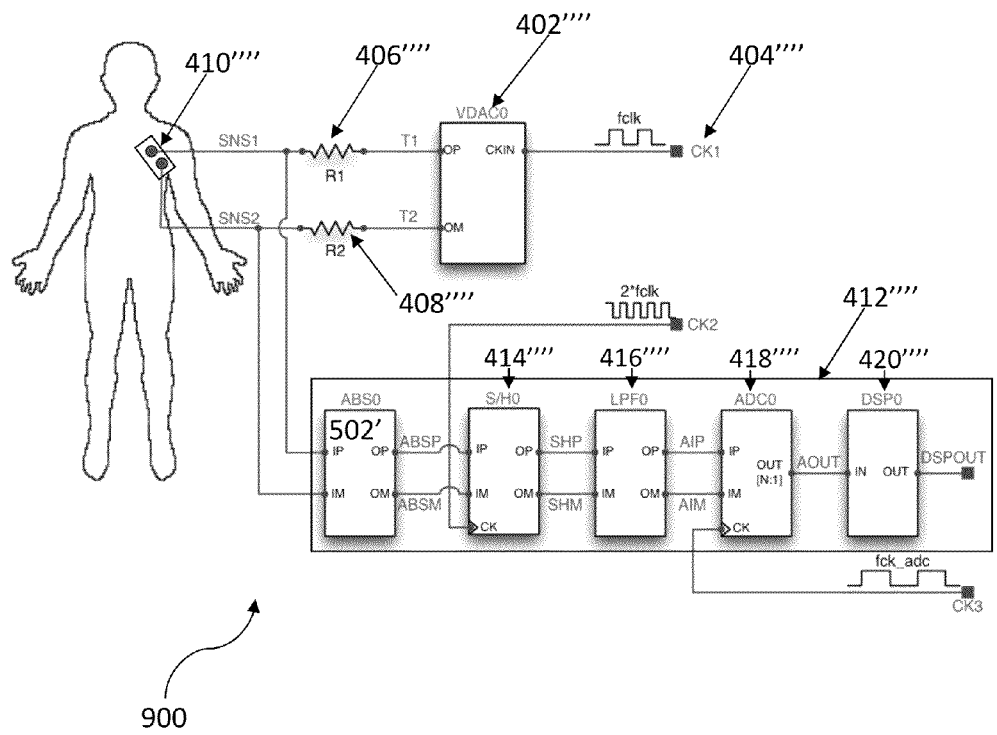
FIG. 9 illustrates a differential system in accordance with a sixth embodiment.

FIG. 9 illustrates a differential system 900 in accordance with a sixth embodiment. The differential system 900 is substantially similar to the differential system 500 except that the order of the ABS0 502' circuit block and the S/H0 414'''' circuit block in the analog/digital signal processing unit 412'''' are reversed. Accordingly, in the differential system 900, the outputs ABSP and ABSM of ABS0 502' are inputted into S/H0 414''''.

If CK2 is timed properly with respect to CK1 by taking into consideration the signal delays throughout the differential system 900 such that the value held by the output of S/H0 414'''' corresponds to the positive amplitude and the rectified negative amplitude of the resultant square or pulsed wave voltage signal and such that information that occurs during the transitions of the ABS0 502' is not passed on, the noise and/or artifacts and/or glitches resulting from the ABS0 502' output can be eliminated to output a cleaner output signal to the rest of the circuit blocks within the analog/digital signal processing unit 412''''.

Figure 10:
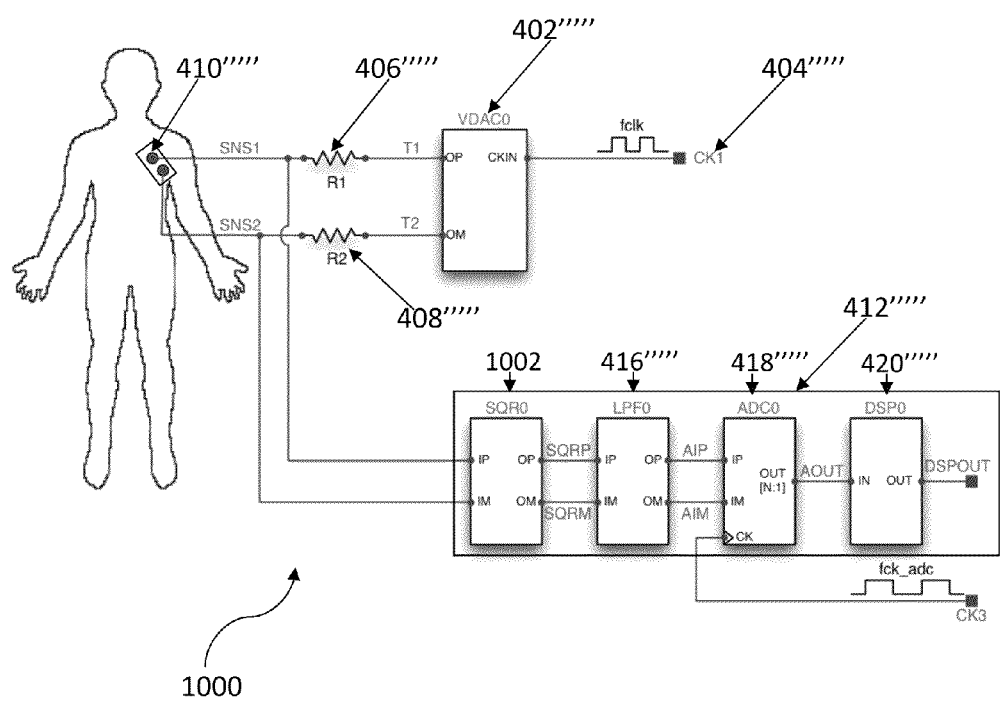
FIG. 10 illustrates a differential system in accordance with a seventh embodiment.

FIG. 10 illustrates a differential system 1000 in accordance with a seventh embodiment. The differential system 1000 is substantially similar to the differential system 400 except that the S/H0 414 circuit block is replaced with a square function circuit block (SQR0) 1002 in the analog/digital signal processing unit 412'''''. Accordingly, in the differential system 1000, the SQR0 1002 takes the square of the resultant square or pulse wave voltage signal instead of the absolute value to output a voltage level corresponding to the amplitude of the resultant square or pulse wave voltage signal that includes some noise and/or transitions. The noise and/or transitions can be eliminated with low pass filtering so the outputs (SQRP and SQRM) of the SQR0 1002 are inputted into the LPF0 416'''' for filtering.

Figure 11:
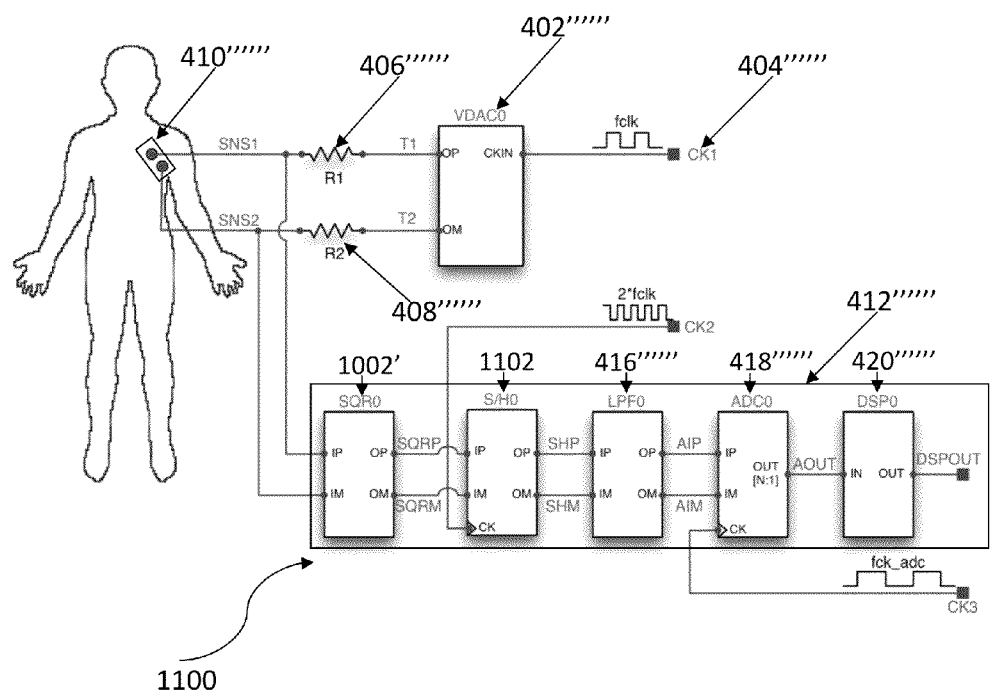
FIG. 11 illustrates a differential system in accordance with an eighth embodiment.

FIG. 11 illustrates a differential system 1100 in accordance with an eigth embodiment. The differential system 1100 is substantially similar to the differential system 1000 except that a S/H0 1102 circuit block is added after the SQR0 1002' block. Accordingly, the noise and/or transitions in the output of the SQR0 1002' block can be further processed by the S/H0 1102 to output a cleaner signal to the LPF0 416'''''.

As above described, the method and system allow for calculating body impedance using a sensor device. By inputting a voltage signal through known impedances and into a sensor device that has been placed on the body of a user, detecting the resultant output voltage signal, and processing the resultant output voltage using a combination of analog and digital signal processing, an accurate body impedance ($Z_{body}$) can be calculated utilizing a non-invasive and efficient system. The calculated body impedance ($Z_{body}$) can be utilized to determine and monitor a variety of health related values including the user's hydration level, respiration rate, and respiration depth.

A method and system for determining body impedance using a sensor device has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for determining a body impedance ($Z_{body}$) of a user, the method comprising:
    coupling a wearable sensor device to the user, wherein the wearable sensor device includes only a first and a second electrode;
    applying a voltage signal ($V_{in}$) through a first impedance ($Z_{in1}$) to the first electrode and through a second impedance ($Z_{in2}$) to the second electrode to produce an output signal;
    measuring a differential voltage ($V_{body}$) across the first and second electrodes using the output signal; and
    calculating the body impedance ($Z_{body}$) using the measured differential voltage ($V_{body}$), the voltage signal ($V_{in}$), the first impedance ($Z_{in1}$), and the second impedance ($Z_{in2}$).

2. The method of claim 1, wherein the voltage signal ($V_{in}$) is a square wave or a pulsed signal with rise and fall times such that the impedance of the first and second electrodes are lower than the body impedance ($Z_{body}$).

3. The method of claim 1, further comprising:
    processing the output signal to improve quality of the measured differential voltage ($V_{body}$) and body impedance ($Z_{body}$) calculation.

4. The method of claim 3, wherein the processing further comprises:
    performing functions on the output signal;
    filtering the output signal;
    digitizing the output signal; and processing the output signal to remove noise and/or artifacts.

5. The method of claim 4, wherein the functions include any of a rectifier, an absolute value, a squaring function, a sample-and-hold function, and a track-and-hold function.

6. The method of claim 4, wherein the filtering is performed by a low pass filter that performs any of analog filtering, analog equalization, and amplification.

7. The method of claim 4, wherein processing the output signal includes performing any of digital filtering using a decimation filter, digital equalizing, digital amplification, artifact removal, and baseline wander removal.

8. The method of claim 4, further comprising:
processing the output signal using user information including any of age, height, race, diet, weight, gender, and distance between the first and second electrode.

9. The method of claim 1, wherein calculating the body impedance ($Z_{body}$) utilizes the following equation:

$$Z_{body} = (V_{body}/V_{in} - V_{body})) \times (Z_{in1} + Z_{in2}).$$

10. The method of claim 9, wherein hydration level of the user $\propto 1/Z_{body}$ and the hydration level is determined by using $Z_{body}$ in conjunction with user information including any of age, height, race, diet, weight, gender, and distance between the first and second electrode.

11. The method of claim 9, wherein air in lungs of the user $\propto Z_{body}$ and respiration rate and respiration depth are determined by monitoring changes in $Z_{body}$ in conjunction with user information including any of age, height, race, diet, weight, gender, and distance between the first and second electrode.

12. A system for determining a body impedance ($Z_{body}$) of a user, the system comprising:
a wearable sensor device coupled to the user, wherein the wearable sensor device includes only a first and a second electrode; and
a voltage generator coupled to the sensor device, wherein the voltage generator applies a voltage signal ($V_{in}$) through a first impedance ($Z_{in1}$) to the first electrode and through a second impedance ($Z_{in2}$) to the second electrode to produce an output signal;
wherein the sensor device measures a differential voltage ($V_{body}$) across the first and second electrodes using the output signal and calculates the body impedance ($Z_{body}$) using the measured differential voltage ($V_{body}$), the voltage signal ($V_{in}$), the first impedance ($Z_{in1}$), and the second impedance ($Z_{in2}$).

13. The system of claim 12, wherein the first impedance ($Z_{in1}$) and the second impedance ($Z_{in2}$) are any combination of resistors, capacitors, inductors, switches, and transformers.

14. The system of claim 12, wherein the voltage signal ($V_{in}$) is a square wave or a pulsed signal with rise and fall times such that the impedance of the first and second electrodes are lower than the body impedance ($Z_{body}$).

15. The system of claim 12, further comprising:
an analog/digital signal processing unit coupled to the sensor device, wherein the analog/digital signal processing unit processes the output signal to improve quality of the measured differential voltage ($V_{body}$) and body impedance ($Z_{body}$) calculation.

16. The system of claim 15, wherein the analog/digital signal processing unit processes the output signal by:
performing functions on the output signal;
filtering the output signal using a filter;
digitizing the output signal using an analog-to-digital converter (ADC); and
processing the output signal using digital signal processing to remove noise and/or artifacts.

17. The system of claim 16, wherein the functions include any of a rectifier, an absolute value, a squaring function, a sample-and-hold function, and a track-and-hold function.

18. The system of claim 16, wherein the filter is a low pass filter and performs any of analog filtering, analog equalization, and amplification.

19. The system of claim 16, wherein processing the output signal using digital signal processing includes performing any of digital filtering using a decimation filter, digital equalizing, digital amplification, artifact removal, and baseline wander removal.

20. The system of claim 12, wherein the body impedance ($Z_{body}$) is calculated utilizing the following equation:

$$Z_{body} = (V_{body}/(V_{in} - V_{body})) \times (Z_{in1} + Z_{in2}).$$

* * * * *